United States Patent [19]

Kontinen et al.

[11] Patent Number: 5,780,261
[45] Date of Patent: Jul. 14, 1998

[54] METHOD AND SYSTEM FOR ENHANCED PRODUCTION OF COMMERCIALLY IMPORTANT EXOPROTEINS IN GRAM-POSITIVE BACTERIA

[75] Inventors: Vesa Kontinen; Matti Sarvas, both of Helsinki, Finland

[73] Assignee: The Finnish National Public Health Institute (KTL), Helsinki, Finland

[21] Appl. No.: 507,391

[22] PCT Filed: Feb. 25, 1994

[86] PCT No.: PCT/FI94/00072

§ 371 Date: Jul. 8, 1996

§ 102(e) Date: Jul. 8, 1996

[87] PCT Pub. No.: WO94/19471

PCT Pub. Date: Sep. 1, 1994

Related U.S. Application Data

[63] Continuation-in-part of Ser. No. 24,154, Feb. 26, 1993, abandoned.

[51] Int. Cl.$^6$ ............ C12P 21/00; C12N 1/21; C12N 15/00; C12N 15/32
[52] U.S. Cl. ............ 435/69.1; 435/320.1; 435/69.8; 435/252.3; 435/252.5; 435/71.1; 435/71.2; 435/252.31; 435/254.11; 935/29; 935/27; 935/48; 935/72; 935/74
[58] Field of Search ............ 435/69.1, 320.1, 435/69.8, 252.3, 252.5, 71.1, 71.2, 252.31, 254.11; 935/29, 27, 48, 72, 74

[56] References Cited

U.S. PATENT DOCUMENTS

| | | |
|---|---|---|
| 4,711,843 | 12/1987 | Chang . |
| 4,879,213 | 11/1989 | Fox et al. . |
| 4,952,508 | 8/1990 | Chang et al. . |
| 4,965,197 | 10/1990 | Liebel et al. . |
| 4,994,379 | 2/1991 | Chang et al. . |

OTHER PUBLICATIONS

Lazar et al (1988) Mol. J. Cell. Biol. vol. 8(3), 1247–1252.
Burgen et al (1990) J. Cell. Biol. vol. 111, 2129–2138.
Wickner, W., Driessen, A.J.M., and Hartl, F. The Enzymology of Protein Translocation Across the *Escherichia coli* Plasma membrane. *Annual Reviews of Biochemistry* 60: 101–124 (1989).

Kontinen, V. and Sarvas, M. Mutants of *Bacillus subtilis* Defective in Protein Export. *Journal of General Microbiology* 134: 2333–2344 (1988).

Kontinen, V. and Sarvas, M. A Gene (prsA) of *Bacillus subtilis* involved in a novel, late stage of protein export. *Molecular Microbiology* 5(5): 1273–1283 (1991).

Haandrikman, A.J., et al. Identification of a Gene Required for Maturation of an Extracellular Lactococcal Serine Proteinase. *Journal of Bacteriology* 171(5): 2789–2794 (1989).

Vos, P. et al. A Maturation Protein is Essential for Production o Active Forms of *Lactococcus lactis* SK11 Serine Proteinase Located in or Secreted from the Cell Envelope. *Journal of Bacteriology* 171(5): 2795–2802 (1989).

Ferrari, F.A., Nguyen, A., Lang, D. and Hoch, J.A. Construction and Properties of an Integrable Plasmid for *Bacillus subtilis*. *Journal of Bacteriology* 154(3): 1513–1515 (1983).

Sibakov, M., Sarvas, M. and Palva, I. Increased secretion of α-amylase from *Bacillus subtilis* caused by multiple copies of α-amylase Gene from *B. amyloliquefaciens* is not further increased by genes enhancing the basic level of secretion. *FEMS Microbiology Letters* 17:81–85 (1983).

Gardel, C., Johnson, K., Jacq, A. and Beckwith, J. The secD locus of *E. coli* codes for two membrane proteins required for protein export. *EMBO Journal* 9(10): 3209–3216 (1990).

*Primary Examiner*—Lila Feisee
*Assistant Examiner*—Khalid Masood
*Attorney, Agent, or Firm*—Virginia H. Meyer, Esq.

[57] ABSTRACT

The invention provides a method and expression system for enhancing secretion of hyperproduced homologous and heterologous exoproteins in gram-positive bacteria such as *Bacillus sp*. The method and system comprise overproduction of PrsA protein in gram-positive bacterial host capable of also overproducing at least one exoprotein of interest. Use of the method and system of the invention results in greatly enhanced secretion of the synthesized exoproteins into the growth medium. Once in the growth medium these secreted exoproteins can be recovered and purified in a straightforward manner.

16 Claims, No Drawings

METHOD AND SYSTEM FOR ENHANCED PRODUCTION OF COMMERCIALLY IMPORTANT EXOPROTEINS IN GRAM-POSITIVE BACTERIA

This application is a continuation in part of U.S. Pat. No. 08/024,154 filed Feb. 26, 1993, abandoned and PCT application PCT/FI94/00072 (WO 94/19471) filed Feb. 25, 1994.

FIELD OF THE INVENTION

This invention relates to a method and expression system for enhanced production of industrially and medically important exoproteins in gram-positive bacteria, especially species of the genus Bacillus.

BACKGROUND

In gram-positive bacteria secreted proteins are exported across a cell membrane and a cell wall, and then are subsequently released into the external medium. On the other hand, gram-negative bacteria are surrounded by two cell (or surface) membranes; they have no cell wall. In gram-negative bacteria, most exported proteins are not released from the cell but stay in the inter-membrane periplasmic space and in the outer membrane.

Two types of components of the secretion machinery have been identified in *E. coli*: soluble cytoplasmic proteins and membrane associated proteins (see for review, Wickner et al., (1991) *Annu. Rev. Biochem.*, 60:101–124). Soluble cytoplasmic proteins, including SecB and heat shock proteins, all prevent the folding of precursors of secreted proteins into a conformation incompatible with secretion. The set of membrane-associated proteins includes the peripheral membrane protein SecA, integral membrane proteins SecY, SecE, SecD, SecF and the signal peptidases Lep and Lsp (reviewed in Hayashi, S. and Wu, H. C. (1990) *J. Bioenerg. Biomembr.*, 22:451–471; Dalbey, R. E. (1991) *Mol. Microbiol.*, 5:2855–2860). These membrane-associated proteins are involved in binding of the precursor and in its translocation across the cytoplasmic membrane, followed by cleavage of the signal peptide and release of the protein.

Knowledge on the secretion machinery of gram-positive bacteria is more limited. The available data on *B. subtilis*, the genetically and physiologically well characterized model organism of the genus, suggest an overall similarity with that of *E. coli*, but also differences in the structure and specificity of individual components, possibly reflecting demands set by the very different composition and architecture of the respective cell envelopes.

Gram-positive bacteria such as *B. subtilis, B. amyloliquefaciens, B. licheniformis* have a very high capacity for secreting proteins, and indeed, many bacillar extracellular enzymes are utilized industrially. Since secreted proteins in gram-positive bacteria are so important commercially, and since the gram-positive secreted proteins traverse through a cell envelope with a very different structure from that of *E. coli* the molecular mechanisms of protein secretion in gram-positive bacteria is of considerable academic and industrial importance.

In this regard we recently discovered a novel component, the PrsA protein, of the secretion machinery of *B. subtilis* (Kontinen, V.P. and Sarvas, M., (1988) *J. Gen. Microbiol.*, 134:2333–2344; Kontinen, V.P., et al., (1991) Mol. Microbiol. 5:1273–1283). The prsA gene, which encodes the PrsA protein, was initially defined by nonlethal mutations that decreased the secretion of several exoproteins (Kontinen, V. P. and Sarvas, M., (1988) *J. Gen. Microbiol.*, 134:2333–2344). Based on the DNA sequence of the cloned prsA gene and our subsequent work with this gene and protein, we assert that prsA encodes a protein (PrsA) that acts as a chaperone, and is translocated across the cytoplasmic membrane (for the initial work, see Kontinen, V. P., etal., (1991) *Mol. Microbiol.* 5:1273–1283). The PrsA protein has been found to possess a limited amount of sequence homology (about 30%) with the PrtM protein of *Lactococcus lactis*, a protein proposed to assist the maturation of an exported serine protease (Haandrikman, A. J., et al, (1989) *J. Bacteriol.*, 171:2789–2794; Vos, P., et al., (1989) *J. Bacteriol.*, 171:2795–2802). A similar function has not been associated with other known proteins of the secretion machinery of bacteria, suggesting that PrsA protein is a novel type of component in the pathway of protein secretion facilitating the release and probably folding of secreted proteins after their translocation across the cytoplasmic membrane in gram-positive bacteria.

It is advantageous to produce proteins of interest in bacteria in secreted form, since exported proteins usually maintain their native conformation, in contrast to intracellular production which, in many cases, results in aggregation of the produced protein. Another advantage of producing industrially and medically important proteins in bacteria in secreted form is that secretion facilitates purification of the protein product. Additionally, unlike *E. coli*, gram-positive bacteria such as *Bacillus sp.* do not contain toxic compounds like lipopolysaccharide, making them especially appropriate hosts for production of medical and pharmaceutical proteins.

Increased yield of secreted proteins would be of great significance for improving the gram-positive bacillar strains used in the industrial production of a number of exoenzymes, such as alpha-amylases, proteases and lipases. The strategy thus far has been to overexpress the appropriate gene. There are known and readily available methods for doing this, such as increasing gene expression by using multicopy plasmids or enhancing the activity of the gene by modifying its regulatory elements, e.g., by using strong promoters, or multiple promoters. Dramatic increases of the synthesis of exoproteins have been achieved this way, up to a level at which increasing the synthesis is of no further benefit because of bottlenecks in the secretion machinery. It would be desirable to increase the capacity of secretion in parallel with increased synthesis. However, to date this has not been possible.

It is an object of the present invention to alleviate the bottleneck of the secretion mechanism in gram-positive bacteria, and to provide a method and a system whereby the levels of proteins normally secreted from gram-positive bacteria such as Bacillus can be enhanced when the expression of a given homologous or heterologous protein of interest has been elevated over the amount normally produced in unmodified or wild type organisms.

It is a further object of the present invention to describe bacterial hosts and plasmids which can be used to enhance the production of a variety of commercially important exoproteins.

SUMMARY

The invention provides a method and expression system for enhancing the levels of homologous or heterologous protein(s) normally secreted from gram-positive bacteria (such as *Bacillus sp.*) when expression of the homologous or heterologous protein(s) has been elevated over unmodified or wild type amounts produced by unmodified or wild type organisms.

The method and system of our invention comprise overproduction of PrsA protein, or a functional homologue thereof, in a gram-positive bacterial host capable of also overproducing at least one homologous or heterologous exoprotein of interest. According to the teaching of the invention, overproduction means an amount greater than wild-type, i.e., more than the amount of the protein (PrsA or a functional homologue thereof, or exoprotein of interest) normally produced by wild type bacteria. Also according to the invention, overproduction is accomplished by standard means known to the art, e.g., use of multicopy plasmids, multiple copies of the genes encoding PrsA, or a functional homologue(s) thereof, and/or the exoprotein of interest, in the chromosome of the host, combined with altering the regulatory elements to increase expression, e.g., use of strong promoter(s), use of multiple promoters, use of enhancers, and so forth. Use of the method and system of the invention results in greatly enhanced secretion, e.g., as much as five to ten fold over controls, of synthesized exoproteins into the growth medium. Once in the growth medium these secreted exoproteins can be recovered and purified in a straightforward manner.

The expression system of the invention comprises a host gram-positive bacteria, e.g., species of Bacillus, capable of expressing greater than wild-type amounts of PrsA protein, or a functional homologue thereof, and greater than wild-type amounts of an exoprotein of interest, e.g., alpha amylase, subtilisin, pneumolysin, lipases, or other exoproteases of commercial interest. The method of the invention comprises using this expression system to enhance production of commercially important exoproteins in gram-positive bacteria. According to the method, at least one exoprotein of interest is overexpressed in a host gram-positive bacteria which also overexpresses (i.e., expresses greater than the amounts produced by wild type bacteria) PrsA protein, or a functional homologue thereof. According to the teaching of the invention, a functional homologue of PrsA protein is a protein which when overexpressed is capable of enhancing the secretory capability of a gram-positive bacteria with respect to secretion of an exoprotein of interest. Also according to the teaching of the invention, a functional homologue of PrsA can be identified by several means including sequence homology to prsA or PrsA, immunological reaction with anti-PrsA antibodies of high titer, and/or functionally, i.e., as a protein which when overexpressed, is capable of enhancing the secretory capability of a gram-positive positive bacteria with respect to secretion of an exoprotein of interest.

A preferred means for transforming host gram-positive bacteria, such as species of Bacilli, so they produce greater than wild-type amounts of PrsA protein is to transform the host with plasmid pKTH277 which carries the prsA gene from *Bacillus subtilis*. Comparable plasmids can be constructed to carry genes which encode functional homologues of the PrsA protein. These plasmids can be used to transform host gram-positive bacteria so they overproduce the functional homologues of PrsA. Once engineered to overproduce PrsA homologues (which can also be referred to as PrsA-like proteins), these host gram-positive strains can be used, according to the teaching of the invention, for enhanced secretion of hyperproduced exoproteins of interest.

The present invention also discloses, and includes, methods and constructs related to our discovery that secretion in gram-positive bacteria can be enhanced by increasing the amount of cellular PrsA protein, or functional homologue(s) thereof, in gram-positive hosts that express greater than wild-type amounts of exoproteins of interest.

In one aspect our invention includes an expression system for enhancing secretion of exoproteins in gram-positive bacteria comprising a gram-positive bacteria capable of expressing greater than wild-type amounts of PrsA protein, or functional homologue(s) thereof, and capable of expressing greater than wild-type amounts of at least one exoprotein of interest.

In another aspect our invention includes a gram-positive bacteria able to express greater than wild-type amounts of at least one exoprotein of interest further comprising pKTH277.

In yet another aspect, our invention includes a gram-positive bacteria able to express greater than wild-type amounts of at least one exoprotein of interest and further comprising at least one of the following: at least two copies of the prsA gene from *Bacillus subtilis*, or a functional homologue thereof; the prsA gene from *Bacillus subtilis*, or a functional homologue thereof, operatively linked to strong regulatory sequences which result in overexpression of said prsA gene, or functional homologue thereof.

Our invention also includes a DNA construct comprising the prsA gene from *Bacillus subtilis*, or a functional homologue thereof, under the control of expression signals which cause overexpression of said prsA gene, or functional homologue thereof, plus a vector further comprising the prsA gene from *Bacillus subtilis*, or a functional homologue thereof, under the control of expression signals which cause overexpression of said prsA gene, or functional homologue thereof.

In yet another aspect our invention includes a method for enhancing secretion of an exoprotein of interest in a gram-positive bacteria comprising expressing greater than wild type amounts of PrsA protein from *Bacillus subtilis*, or a functional homologue thereof in the gram-positive bacteria, wherein the gram-positive bacteria is also capable of expressing greater than wild type amounts of the exoprotein.

Still further the invention includes a method for creating an improved non-*Bacillus subtilis* gram-positive host organism useful for enhanced secretion of an exoprotein of interest that is overexpressed in the host organism, the method comprising (a) identifying a gene from the host organism that encodes a functional homologue of PrsA protein from *Bacillus subtilis*, and (b) enhancing the expression of the gene identified in step (a) by at least one of the following: introducing into the host organism at least one additional copy of the gene; introducing into the host organism the gene operatively linked to expression sequences which result in overexpression of the gene.

The invention also includes a method for identifying a gene which encodes a functional homologue of PrsA from *Bacillus subtilis*, the method comprising identifying, by means of Southern blotting, DNA which hybridizes with DNA probe(s) from the prsA gene from *Bacillus subtilis*, and demonstrating that the gene encodes a protein which when overexpressed, is capable of enhancing the secretory capability of a gram-positive bacteria with respect to secretion of an exoprotein of interest.

Still further, the invention includes a method for identifying a gene which encodes a functional homologue of PrsA from *Bacillus subtilis*, this method comprising identifying protein that reacts with anti-PrsA antibod(ies) of high titer, and demonstrating that when the protein is present in greater than wild-type amounts in a gram-positive bacteria, the protein is capable of enhancing the secretory capability of the gram-positive bacteria with respect to secretion of an exoprotein of interest.

These and other features, aspects and advantages of the invention will become better understood with reference to the following description, examples, methods and materials, and appended claims.

DESCRIPTION

When the expression level (synthesis) of an exported protein is high in gram-positive bacteria such as *Bacillus sp.*, the capacity of the secretion apparatus is a limiting factor in protein secretion and production of these proteins in secreted form. Our invention provides a system and method for overcoming this limitation or bottleneck.

Our invention is based on our initial surprising discovery that secretion in gram-positive bacteria such as species of Bacillus can be enhanced by increasing the amount of only one component of the bacillar export machinery, i.e., the amount of cellular PrsA protein, or functional homologues thereof, in gram-positive bacterial hosts that express greater than wild-type amounts of exoproteins of interest. The method and system of the invention are useful regardless of how the proteins of interest are overproduced in the gram-positive bacterial host. Thus the method and system can be used to improve a variety of overproducing commercial strains now used in industrial applications.

The method and system of the invention can be used with any gram-positive bacteria. Bacteria of the genus Bacillus are preferred. Especially preferred are *Bacillus alkalophilus, Bacillus amyloliquefaciens, Bacillus brevis, Bacillus circulans, Bacillus coagulans, Bacillus lautus, Bacillus lentus, Bacillus licheniformis, Bacillus stearothermophilus, Bacillus subtilis,* and *Bacillus thuringiensis*.

The method and system of the invention can also be used with any desired exoprotein of interest. Examples of exoproteins of interest that may be produced according to the method and system of the invention are listed below, where the exemplary exoproteins are presented by general categories.

Antigenic proteins of microbes and protozoa: Capsule, outer membrane and fimbria proteins from any gram negative bacteria, but especially those from: *Bacteroides fragilis, Fusobacterium spp., Bordetella pertussis, Haemophilus influenzae, Yersinia enterocolitica, Yersinia pestis, Branhamelila catarrhalis, Escherichia coli, Klebsiella pneumonia, Vibrio cholerae, Proteus mirabilis, Pseudomonas aeruginosa, Serratia marcescens, Legionella pneumophila, Neisseria gonorrhoeae, Neisseria meningitidis, Salmonella typhimurium, Salmonella typhi, Salmonella pararyphi B. Mycobacterium tyberculosis, Chlamydia trachomatis,* and *Shigella spp.*

Protein toxins or secreted proteins from any bacteria, but especially those from: *Staphylococcus aureus, Pseudomonas aeruginosa, Clostridium spp., Escherichia coli, Yersinia pestis, Vibrio cholerae, Bordetella pertussis*, M-Protein of the *Streptococcus pyogenes* bacterium, Excreted enzymes of *Stretococcus mutans*.

Surface proteins of any microorganism, but especially those from the following microorganisms (in all phases of development): *Plasmodium spp., Toxoplasma spp., Leishmania spp., Schistosoma spp., Trypanosama spp.* Adhesion protein of *Streptococcus sp.*, and adhesion protein of *Staphylococcus aureus*.

Antigen proteins or viruses: HA and NA proteins of myxoviruses (influenza A H1–H12, influenza B, influenza C): HN and F proteins of paramyxoviruses (parainfluenze 1–4, Newcastle disease virus, Measles virus, Respiratory syncytial virus, Parotitis virus, Distemper virus): G protein of Rabies virus; E1 and E2 proteins of alfaviruses (Chikungunya, Western, Easter, Venezuelan equine encephalitis virus, O'nyong-nyong virus, Semliki Forest virsu, Sindbis virus); V1 and V3 proteins of flavin viruses (Denque 1–4, Japanese encephalitis virus, Mite encephalitis viruses, Murray Valley encephalitis virus, Kyasanur Forest disease virus, Looping ill virus, Omsk hemorrhagic fever virus); surface proteins of German measles virus; surface proteins of Hog Cholera virus; surface proteins of Equine arthritisvirus; G1 and G2 proteins of Bunya viruses (Rift Valley fever virus, Crimean hemorrahagic fever virus, California encephalitis virus, Phlebotomus fever virus); G1 and G2 proteins of arena viruses (Lassa fever virus, Lymphocytic chorion meningitis virus); proteins V1–V4 of picorna viruses (polio 1–3, Coxsackie A viruses 1–24, Coxsackie B viruses 1–6, ECHO viruses 1–8, 11–34, hepatitis A virus, hepatitis B virus, hepatitis C virus, Human rhino viruses 1–113); surface proteins of rota viruses; surface proteins of herpes viruses (HSV 1, 2, Cytomegalo virus, Epstein-Barr virus, Equine abortion virus); VP1–VP3 proteins of papova viruses (BK virus, Human wart virus); p proteins of parvo viruses (mink enteritis virus, Bovine parvo virus, Feline parvo virus, Procine parvo virus); structure proteins of Human hepatitis B virus; surface proteins of Ebola and Marburg viruses; and Hexone, pentone and fiber proteins of adeno viruses, (Human adeno viruses 1–33).

Industrial enzymes: With regard to industrially important enzymes, such enzymes may be amylolytic, lipolytic and proteolytic enzymes, carbohydrases, transferases, isomerases, peroxidases, oxidoreductases, oxidases etc. More specifically, the enzyme of interest may be a protease, a lipase, a cutinase, an amylase, a galactosidase, a pullulanase, a cellulase, a glucose isomerase, a protein disuphide isomerase, a CGT'ase (cyclodextrin gluconotransferase), a phytase, a glucose oxidase, a glucosyl transferase, laccase, bilirubin oxidase, or a xylanase. Examples include, but are not limited to: alpha-amylase, amino acid acylase, amyloglucosidase, bromelain, phisine, beta-galactosidease, beta-gulcanase, glucose-ismorase, glucoseoxidase, hemicellulase, invertase, catalase, collagenase, xsylanase, lactase, lipase, naringinase, pancreatin, papain, pectinase, penicillinamidase, pepsin, protease, pullulanase, isoamylase, rennin, ribonuclease, cellulase, streptokinase and trypsin.

Exoproteins of medical interest can also be produced. Such proteins include diagnostic antigens, proteins that can be used as vaccines, and pharmaceuticals.

According to the teaching of the invention, the exoproteins of interest need not be native exoproteins, but instead can be novel proteins that have been designed and created to be exoproteins using genetic engineering techniques. For example, a normally non-secreted protein from one species (or an engineered non-native protein) can be engineered to be an "exo" protein by adding a signal sequence to the sequence encoding the structural protein. This engineered exoprotein can be expressed in a gram-positive bacteria such as a species of *Bacillus*, which overexpresses PrsA protein, or a functional homologue thereof. In this way the method of the invention can be used to enhance secretion of these non-native or engineered proteins of interest.

Turning now to aspects of our invention, to illustrate one embodiment of our invention we show the effect overexpression of the prsA gene from *Bacillus subtilis* has on the secretion of the two important industrial exoenzymes of *Bacilli*, alpha-amylase and subtilisin. For these studies, a 5.3 kB insert, containing the entire prsA gene from *Bacillus subtilis*, was cloned into a low copy number shuttle plasmid (pKTH277), which was then used to introduce additional copies of prsA into *Bacillus subtilis*. (The DNA and deduced amino acid sequences of the prsA gene from *Bacillus subtilis* appear in the EMBUGenBank/DDBJ Nucleotide Sequence Data Libraries under the accession number X57271.) (pKTH277 was obtained by ligating the 5.3 kB EcoRI- BamHI fragment from pKTH268 with low copy number shuttle plasmid pHP13 linearized by digestion with respective restriction enzymes and transforming into the *E. coli* strain TG1. The sizes of pKTH268 and pKTH277 are 8.5 kB and 10.2 kB, respectively. See also Kontinen, et al., (1991) *Mol. Microbiol.*, 5:1273–1283, which is incorporated by reference herein). The presence of pKTH277 in *B. subtilis* increased the amount of the protein corresponding to the PrsA protein by approximately 10-fold over the wild type. When the genes for different secreted proteins are expressed in strains of Bacillus containing these increased levels of PrsA protein, the level of protein secreted into the culture medium is increased substantially. For example, the secretion of alpha-amylase of *Bacillus amyloliquefaciens* was found to be increased by 2.5-fold in this system, the secreted level of the thermoresistant alpha-amylase of *Bacillus licheniformis* was elevated by six-fold, and subtilisin (alkaline protease) from *Bacillus licheniformis* was secreted at two times the control level.

In these studies the exoenzymes were overexpressed in host strains in amounts likely to saturate the secretion machinery, either by placing the gene which encoded the exoprotein on a multicopy plasmid or inserting it in the chromosome of the host. (In these studies, all multicopy plasmids coding for the exoenzymes were derivatives of pUB 110, which belongs to a different incompatibility group than the shuttle plasmid pKTH277, allowing their replication in the same host cell. The stability of these plasmids was further increased in most cases by using a recE4 host strain, which prevents efficient recombination between homologous sequences (Dubnau et al., 1973; Keggins et al., 1978).

The first exoenzyme studied to illustrate this aspect of our invention was alpha-amylase of *B. amyloliquefaciens* (AmyE) encoded by pKTH10 (Palva, I. (1982a) Gene, 19:81–87; Palva, I., et al., (1982b) *Proc. Natl. Acad. Sci. USA*, 79:5582–5586). We found that in the wild-type strain hyperproducing this alpha amylase, the presence of pKTH277 indeed enhanced the secretion of alpha-amylase throughout the stationary phase of growth, about 2.5–3 fold over the level of the control strain which did not overexpressing PrsA. The highest concentration of alpha amylase in the culture supernatant (about 3400 micrograms/ml) was found after the growth of 24 hours. In the absence of pKTH277, the strain secreted only 1200 micrograms/ml. Qualitatively similar results were obtained when alpha-amylase was expressed from one copy of the amyE gene, which was inserted in the chromosome and transcribed at high level due to modified regulation.

The second exoprotein we tested was the thermoresistant alpha-amylase of *B. licheniformis* (AmyL), the major liquefying alpha-amylase of industrial importance (Ortlepp et al., 1983; Diderichsen, B., et al., (1991) *Res. Microbiol.*, 142, 793–796). Secretion of this enzyme in *B. subtilis* at amounts comparable with those of the alpha amylase of *B. amyloliquefaciens* was achieved by expressing the appropriate gene from the secretion vector based on the promoter and signal sequence of the gene of the latter enzyme (Palva, I. (1982) Gene, 19:81–87; Palva, I., etal., (1982) *Proc. Natl. Acad. Sci. USA*, 79:5582–5586); Sibakov, M. (1986) *Eur. J. Biochem.*, isS, 577–581). Introduction of pKTH277 into one such strain (to result in IH6760) increased the amount of alpha-amylase in the culture medium about six fold, with the same difference seen from late exponential stage to cultures of 45 hours.

Alkaline protease, subtilisin, is a different type of exoprotein, whose precursor contains in addition to the signal sequence a further extension, the prosequence (Wells, etal., (1983) *Nucleic Acids Res.*, 11:7911–7925; Wong, S.-L., et al., (1984) *Proc. Natl. Sci. USA*, 81:1884–11188). The effect of an increased amount of PrsA on this secretion was studied by comparing two strains, one with increased level of PrsA (IH6789), another one with the wild type level. Both secreted the heterologous subtilisin of *B. licheniformis* (SubC, which is used as a laundry powder and is an important industrial product) coded by the multicopy plasmid pMJ57 (Hastrup, S. and Jacobs, M. F. (1990) In Zukowski, M. M., et al., (eds.), *Lethal phenotype conferred by xylose-induced overproduction of apr-lacZ fusion protein*, vol. 3, Academic Press, Inc., San Diego, Calif., pp. 33–41). In this plasmid the subC gene is under the control of a xylose inducible promoter. Comparison of the secretion of subtilisin from the two strains, when fully induced, showed that its amount in the culture supernatant of IH6789 (increased amount of PrsA) was about twofold higher than that of the control IH6788 at all time points assayed.

We also studied the effect of pKTH277 on the natural low level secretion of endogenous exoenzymes in a strain devoid of any plasmid causing hypersecretion. The amount of secreted alpha amylase and total proteases in the late exponential phase of growth or in overnight cultures was the same in strains carrying pKTH277 or the cloning vector pHP13. Based on these results it appears that the increased amount of PrsA protein enhances secretion of hyperproduced exoenzymes only.

In order to confirm the role of PrsA in the enhancement caused by the 5.3 kb fragment in the above plasmids, we inactivated the prsA gene in the plasmid pKTH277 by insertions in the EcoRV site of its prsA gene (at the nucleotide 382). In pKTH3261 the insert was a 560 bp fragment of the blaP gene of *B. licheniformis* flanked by translational stop codons, and in pKTH3262 a 4.6 kb EcoRV fragment of phage lambda. SDS-PAGE analysis of whole cell proteins of *E. coli* carrying these plasmids showed no full-size PrsA protein expressed by either plasmid, and a putative truncated PrsA of the expected size (14 kDa) expressed by pKTH3261 (data not shown). As a control, we constructed pKTH3253 in which the 5.3 kbp fragment was truncated for 1.9 kbp downstream of prsA, leaving this gene intact. In *B. subtilis* (IH6624 carrying pKTH10) the two plasmids with an insertion in prsA did not enhance the secretion of alpha amylase, while pKTH3253 did.

Enhanced secretion obtained by overproduction of prsA is of obvious advantage for large scale industrial production of exoenzymes. In such applications it is sometimes desirable to avoid the use of potentially unstable multicopy plasmids. One strategy is to insert one or few copies of the structural gene of the exoenzyme in the chromosome, combined with altering its regulatory elements to increase expression. We therefore tested the effect of PrsA overproduction on the secretion of alpha amylase in such a system, where one copy of amyE was inserted in the chromosome fused to the target sequence of the regulatory protein DegQ in a strain overexpressing DegO (A. Palva, personal communication). Also in this strain the high level of alpha-amylase secretion was enhanced about three fold by increasing the amount of PrsA protein (Table 1, strains BRB764 and IH67703). This indicates that the enhancement of secretion is achieved when the starting level of expression of exoprotein is high, regardless of the way the increased expression of the target gene has been obtained.

Turning now to the presence of PrsA in gram-positive bacteria other than *Bacillus subtilis*, we have confirmed the presence of PrsA or PrsA homologues in other species, e.g., *Bacillus amyloliquefaciens* and *Bacillus licheniformis*. The amount of PrsA protein in *Bacillus amyloliquefaciens* is similar to the amount in *Bacillus subtilis* cells, while the amount of PrsA protein in *Bacillus licheniformis* cells appears to be less. In addition, the components of the secretion machinery in these gram-positive bacillar strains are similar to that of *Bacillus subtilis*. *Bacillus amylolique-*

*faciens* and *Bacillus licheniformis* are two of the most widely used species of Bacillus in large scale industrial processes for the production of secreted proteases and amylases. The method of the invention using overproduction of PrsA protein to increase secretion of homologous and heterologous exoproteins of interest is especially useful in these strains.

As part of our invention we also teach how PrsA protein and/or the prsA gene can be identified in other gram-positive bacteria, and that functional homologues of the PrsA protein from *Bacillus subtilis* exist and can be used in the method and system of the invention. Functional homologues of the PrsA protein from *Bacillus subtilis* can be identified in other gram-positive positive species by using anti-PrsA antibody of high titer. Alternatively, the prsA gene or homologous prsA-like genes which encode functional homologues of the PrsA protein from *Bacillus subtilis* can be identified by Southern blotting using probe(s) from the prsA gene, or a prsA-gene fragment. If the PrsA-like protein is found to exist, but there is insufficient homology to the prsA gene or PrsA protein to be detected unequivocally with antibodies specific for the PrsA protein, or DNA probes containing sequences homologous to the prsA gene, the homologous gene can be located and cloned, so unequivocal identification can be made.

However, in most cases homologous proteins and genes can be found using antibodies specific for the PrsA protein, or DNA probes containing sequences homologous to the prsA gene. For immunological identification, immunoblotting (Western blotting) can be used to detect the PrsA protein with anti-PrsA antibody of high titer. The antiserum is produced by immunizing an appropriate animal (e.g., rabbit) with PrsA protein of *B. subtilis*, or preferably with a PrsA protein homologue of another species more closely related to the species of interest than *B. subtilis*. To identify the PrsA, the bacterium of interest can be grown on a number of growth media, but preferably, the bacterium is grown on a medium where there is minimal induction of proteases. Bacterial cells are collected, again preferably at a growth phase with minimal amount of proteases present, and broken with a method appropriate for the species (usually a combination of enzymatic treatment and mechanical disrupture with sonication, French pressure cell, or shearing with glass beads). Samples of various sizes of broken cells and particulate fraction of the disrupted whole cells, prepared with ultracentrifugation, are electrophoresed in SDS-PAGE with standard methods, proteins are transferred to membrane filters and detected with anti-PrsA antiserum and the labeled second antibody. (Smaller amounts of PrsA protein can be detected if the particulate fraction is prepared). In all these steps standard methods and commercial reagents can be used.

To identify the prsA gene, or a prsA-like gene that encodes a functional homologue of PrsA in a species of interest, Southern blotting can be used. In this method, appropriate DNA probes from the prsA gene are hybridized to/with appropriately fragmented and electrophoresed chromosomal DNA of the species of interest according to the standard method of Southern hybridization. The hybridization probe may be any fragment of DNA containing the prsA gene of *B. subtilis*, or a fragment of this gene, or a DNA fragment containing the prsA gene homologue of another species or a fragment of that gene. Once identified, the prsA gene homologue can be sequenced to further confirm its identity.

The teaching of the present invention includes not only overexpression of the PrsA protein of *Bacillus subtilis*, but also overexpression of a functional homologue of the PrsA protein from *Bacillus subtilis* in a gram-positive species of interest. According to the teaching of the invention, either the prsA gene of *B. subtilis* or the prsA gene homologue from another species, including the host species, is introduced into the host species. The prsA gene or its homologue is brought under the control of expression signals which are active in the species of interest in order to result in the high level (but not lethal) expression of the prsA gene. This can be accomplished in a variety of ways, including:

(1) The transfer of the plasmid pKTH277 to the species of interest. The transfer can take place with any method of transformation applicable to that species, like transformation, transduction, protoplast transformation, electroporation or conjugation. pKTH277 is maintained as multiple copy plasmid in many other gram-positive species other than Bacillus, and the expression signals of the prsA gene in that plasmid are active in many gram-positive species.

(2) Inserting the 5.3 kb SacI fragment of pKTH277 into any other plasmid compatible with the species of interest and maintaining it at suitable copy number for high, but not lethal level of expression of prsA, relative to the activity of the prsA gene of *B. subtilis* in that species. The plasmid is then transferred to that species using any method of transformation applicable to that species. Alternatively, the fragment of DNA inserted into the plasmid can contain a prsA gene homologue of another species with its expression signals.

(3) Inserting the DNA fragment of pKTH277 encoding the signal sequence and the mature part of the PrsA protein to an expression vector suitable for the species of interest, under the control of expression signals in that plasmid to achieve high level expression of prsA. As above, the appropriate fragment may derive from a prsA gene homologue of another species.

(4) The DNA constructions of paragraphs (2) and (3) above can be inserted into the chromosome of the species of interest instead of a plasmid. In that case, expression signals have to be chosen which are active enough to ensure high level expression of PrsA although there is only one copy of the gene per the genome.

As inventors who are also basic scientists, by design and of necessity much of our work is done under laboratory or simulated industrial conditions. However, with the help of industrial collaborators, it has been shown that the method and system of our invention work very well with commercially useful bacterial stains, under industrial fermentation conditions.

Methods and materials used in our studies, and examples of our invention are included below to further aid those skilled in the art in practicing the method and system of our invention.

MATERIALS AND METHODS

Bacterial Strains and Plasmids prs mutants of *Bacillus subtilis* Marburg 168 and their parent strains are shown in Table 1. Listed are also *B. subtilis* and *E. coli* strains overexpressing PrsA protein and *B. subtilis* strains with enhanced secretion of exoenzymes due to increased cellular amount of PrsA protein and their appropriate control strain. *E. coli* strains used as cloning hosts with plasmid vectors were HB101, TG1 and DH5α (Sambrook J., et al., (1989) *Molecular cloning. A laboratory manual.* Cold Spring Harbor Laboratory Press, Cold Spring Harbor, N.Y.) and with lambda, Kw25 1 (Promega, Madison, Wis.).

pHP13 (Haima, P., etal., (1987) *Mol. Gen. Genet.*, 209:335–342, pJH101 (Ferrari, F. A., et al., (1983) *J Bacteriol.*, 154:1513–1515), pGEM3zf(+) (Promega) and pDR540 (Pharmacia, Upsala, Sweden) were used as cloning vectors for prsA gene and its fragments. Properties of these plasmid vectors and constructed derivative plasmids carrying the prsA gene with a 5.3 kb (pKTH277 and pKTH268) or 3.4 kb (pKTH3253) insert are shown in Table 2. The prsA gene in pKTH3253 was disrupted by inserting a fragment either from *B. licheniformis* blaP gene (0.5 kb) or bacteriophage lambda genome (4.6 kb) in the unique EcoRV site in the ORF of prsA (the resulted plasmids were pKTH3261 and pKTH3262). pKTH10 (Palva, I. (1982a) *Gene*, 19:81–87; Palva, I., et al., (1982b) *Proc. Natl. Acad. Sci. USA*, 79:5582–5586) and pMJ57 (Hastrup, S. and Jacobs, M. F. (1990) In Zukowski, M. M., et al., (eds.), *Lethal phenotype conferred by xylose-induced overproduction of apr-lacZ fusion protein*, vol. 3. Academic Press, Inc., San Diego, Calif., pp. 33–41) are multicopy plasmids producing large amounts of *B. amyloliquefaciens* alpha-amylase (AmyE) and *B. licheniformis* subtilisin (SubC) secreted into the external medium, respectively. pKTH1582 has been constructed cloning the amyL gene from *B. licheniformis* on a secretion vector system of *B. subtilis* (BRB360 in Sibakov, M. (1986) *Eur. J. Biochem.*, 1sS, 577–581; Palva, I. (1982a) *Gene*, 19:81–87; Palva, I., et al., (1 982b) *Proc. Natl. Sci. USA*, 79:5582–5586).

Growth Media and Culture Conditions

Bacteria were grown in modified L-broth (1% tryptone, 0.5% yeast extract, 0.5% NaCl) with shaking at 37 degrees C., or on L-plates containing 1.5% agar (Difco, Detroit, Mich.) with appropriate antibiotics at +37 degrees C. (Kontinen, V. P., et. al., (1991) *Mol. Microbiol.* 5:1273–1283); plates were modified for alpha amylase (5% starch and 2.5% agar) and subtilisin overexpressing strains (0.2% xylose and 1% milk powder). L-broth was supplemented with 2% soluble starch (Merck, Darmstadt, Germany) or used as 2-fold concentrated medium for production of exoenzymes. Strains producing subtilisin were grown on L-plates containing 1 % milk powder. The production of exoenzymes was studied in two-fold concentrated L-broth with vigorous shaking. The growth was indicated by turbidity of the culture measured with KlettSummerson colorimeter (Klett Manufacturing Co., Inc. N.Y.) using a no.66 filter.

Enzyme Assays

Alpha amylase was assayed with Phadebas tablets (Pharmacia) as described in Kontinen, V. P. and Sarvas, M., (1988) *J. Gen. Microbiol.*, 134:2333–2344. For the plate assay bacteria were streaked on L-plate containing 5% of starch, and the halo around colonies was measured after incubation of the plates at 4 degrees C. Typically, there was no zone around wild-type colonies producing endogenous alpha amylase, while that of strains carrying pKTH10 was more than 2 mm depending on the age of plates. Subtilisin of *B. licheniformis* and chromosomally-encoded proteases were assayed in 1 ml of 0.1M Tris-0.0 1M CaCl2 (pH 8.0) with a chromogenic peptide substrate succinyl-AlaAla-Pro-Phe-p-nitroanilide (Del Mar, E.G., et al., (1979) *Anal. Biochem.*, 99:316–320). The rate of hydrolysis was measured on a Hewlett Packard diode array spectrophotometer at 410 nm. To determine the specific activities of alphaamylases and subtilisin their amount in a sample of culture supernatant was estimated either as in ((Kontinen, V. P. and Sarvas, M., (1988) *J. Gen. Microbiol.*, 134:2333–2344) or with SDS-PAGE stained with Coomassie Blue. The enzyme amounts were expressed as micrograms/ml.

TABLE 1

Bacterial strains

| Strain | Relevant genotype and properties | Parent strain, source or reference |
|---|---|---|
| *B.subtilis* | | |
| IH6064 | metB5 sacA321 | (Sibakov et al., 1983) |
| IH6090 | his metBS sac321 | IH6064 |
| IH6157 | IH6090 (pKTH10) | IH6090 |
| IH6160 | IH6064 (pKTH10) | IH6064 |
| IH6480 | prs-3 metB5 sacA321 (pKTH10) | IH6157 |
| IH8482 | prs-29 metB5 sacA321 (pKTH10) | IH6157 |
| IH6483 | prs-33 metB5 sacA321 (pKTH10) | IH6 157 |
| IH6484 | prs-40 metB5 sacA321 (pKTH10) | IH6157 |
| IH6485 | prs-3 metB5 sacA321 | IH6480 |
| IH6487 | prs40 metB5 sacA321 | IH6484 |
| IH6489 | prs-II metB5 sacA321 (pKTH10) | IH6160 |
| IH6491 | prs-13 metB5 sacA321 (pKTH10) | IH6160 |
| IH6494 | prs-33 metB5 sacA321 | IH6483 |
| IH6497 | prs-26 metB5 sacA321 (pKTH10) | IH6157 |
| IH6498 | prs-13 metB5 sacA321 | IH6491 |
| IH6501 | prs-26 metB5 sacA321 | IH6497 |
| IH6504 | prs-II metB5 sacA321 | IH6489 |
| IH6513 | QB917 (pKTH10) | QB917 |
| IH6521 | prs-13 hisAl trpC2 (pKTH10) | IH6513 |
| IH6523 | prs-II metB5 sacA321 (pKTH10) | IH6513 |
| IH6622 | IH6624 (pKTH277) | IH6624 |
| IH6623 | IH6624 (pHP13) | IH6624 |
| IH6624 | PSLI (pKTH10) | PSLI |
| IH6654 | prs-29 metB5 sacA321 | IH6482 |
| IH6752 | PSLI (pMJ57) | PSLI |
| IH6755 | PSLI (pHP13) | PSLI |
| IH6757 | PSLI (pKTH1582) | PSLI |
| IH6759 | IH6755 (pHP13) | IH6755 |
| IH6760 | IH6757 (pKTH277) | IH6757 |
| IH6770 | BRB764 (pKTH277) | BRB764 |
| IH6774 | IH6160 (pKTH277) | IH6160 |
| IH6788 | IH6752 (pKTH3229) | IH6752 |
| IH6789 | IH6752 (pKTH3230) | IH6752 |
| PSLI | arg(GH)15, leuA8, rm-, recE4, stp, thrA | IA510 in BGSC |
| QB917 | hisAl thr-5 trpC2 | IAIO in BGSC |
| BRB764 | ::φ(P$_{subs}$-amyE) (pKTH1743) | A. Palva, University of Helsinki |
| *B.subtilis* | | |
| IH6559 | prsA29, recE4, trpC2 (::pKTH1601) | Kontinen et al, 1991 |
| IH6799 | IH6064 (::pKTH3200) | IH6064 |
| IH6811 | IH6624 (pKTH3253) | IH6624 |
| IH6812 | IH6624 (pKTH3261) | IH6624 |
| IH6813 | IH6624 (pKTH3262) | IH6624 |
| *E. coli* | | |
| EH1568 | HBIOI (pKTH268) | HBIOI |
| EH1581 | DH5α (pKTH3101) | DH5α |
| EH1631 | TGI (pKTH3180) | TGI |
| EH1639 | TGI (pGEM3zf(+)) | TGI |
| EH1640 | TGI (pDR540) | TGI |
| EH1674 | TGI (pKTH277) | TGI |
| EH1675 | TGI (pKTH3253) | TGI |
| EH1678 | TGI (pKTH3261) | TGI |
| EH1 679 | TGI (pKTH3262) | TGI |

1) pKTH1743 is a dreivative of pUB110 carrying a 0.3 kbp insert with an ORF for *B. subtilis* decQ gene 2) The Bacillus Genetic Stock Center, The Ohio State University, Ohio

TABLE 2

Plasmids

| Plasmid number | Cloned genes and resistance markers | Derivative of (Source and/or references) |
|---|---|---|
| pKTH10 | amyE neo | pUB110 (Palva, 1982; Gryczan et al., 1978) |
| pKTH268 | prsA bla | pGEM3zf(+) (Promega; Sambrook et al., 1989) |
| pKTH277 | prsA cat ermC | pHP13 (Haima et al., 1987) |
| pKTH1582 | amyL neo | pUB110 (I. Palva: Sibakov, 1986) |
| pKTH1743 | degQ neo | pUB110 (A. Palva) |
| pKTH1786 | bla cat neo | pAMβI (M. Simonen; Leblanc and Lee, 1984) |
| pKTH3101 | 'prsA bla | pKTH268 |
| pKTH3180 | O/P$_{tac}$-'prsA bla | pDR540 (Pharmacia) |
| pKTH3229 | ermC | pHP13 |
| pKTH3230 | prsA ermC | pKTH3229 |
| pKTH3253 | prsA cat ermC | pHP13 |
| pKTH3261 | 0.5 kb insert in prsA cat ermC | pKTH3253 |
| pKTH3262 | 4.5 kb insert in prsA cat ermC | pKTH3253 |
| pJH101 | bla cat tet | (Ferrari et al., 1983) |
| pMJ57 | O/P$_{xyn}$-'subC cat | pUB110 (Hastrup and Jacobs, 1990) |

EXAMPLES

Example 1

Enhancement of Alpha Amylase Secretion in *B. subtilis* when there is an Increased Amount of PrsA Protein The following table (Table 3) illustrates enhancement of α-amylase secretion in *Bacillus subtilis* under various conditions when the host gram-positive bacteria also overexpresses PrsA protein.

TABLE 3

Enhancement of α-amylase secretion in *B. subtilis* by overexpression of PrsA protein

| Strain No. | α-amylase expressed from a gene in | The plasmid PrsA was expressed from Plasmid No. | prsA gene in the plasmid | α-amylase secreted μg/ml[c] |
|---|---|---|---|---|
| IH6160 | Multicopy plasmid[a] | — | | 1000 |
| IH6774 | Multicopy plasmid[a] | pKTH277 | Intact | 3100 |
| BRB764 | Chromosome[b] | — | | 630 |
| IH6770 | Chromosome[b] | pKTH277 | Intact | 2000 |
| IH6811 | Chromosome[b] | pKTH3253 | Intact | 3700 |
| IH6812 | Multicopy plasmid[a] | pKTH3261 | Disrupted | 1300 |
| IH6813 | Multicopy plasmid[a] | pKTH3262 | Disrupted | 1400 |

[a] pKTH10 with amyE of *B. amyloliquefaciens*
[b] One copy of amyE under a promoter of increased activity
[c] The α-amylase activity of culture supernatant was assayed in the late stationary phase of growth

Example 2

Enhancement of Alpha Amylase Secretion in *B. amyloliquefaciens* when there is Hyperexpression of PrsA Protein This example demonstrates the effect of overproduction of PrsA protein of *B. subtilis* in *B. amyloliquefaciens* when the host gram-positive bacteria also hyperexpresses PrsA protein.

ALK02732 is a derivative of ALK02100 and contains the multicopy plasmid pKTH10 encoding the a-amylase of *B. amyloliquefaciens*. The strain thus contains tens of copies of a-amylase gene, and secretes about 20 fold more α-amylase than the wild type strain ALK02100 (Vehmaanperäetal., *J. Biotechnol.* 1991,19,221–240). Immunoblotting of cells of ALK02732 with anti PrsA antiserum showed that the amount of PrsA protein was similarly small in ALK02732 as in ALK02100, which is referred to below. Thus PrsA is rate limiting for protein secretion in ALK02732.

The plasmid pKTH277 was transferred with electroporation to the *B. amyloliquefaciens* strain ALK02732 to make ALK02732(pKTH277). The amount of PrsA in ALK02732 (pKTH277) was many folds higher than in ALK02732, as determined with immunoblotting. This is in good agreement with the similar increase of PrsA proteins in *B. subtilis* strains transformed with PKTH277.

The amount of α-amylase secreted to the growth medium (Luria broth of double strength with 2% of soluble starch) by ALK02732 and ALK02732(pKTH277) were determined during logarithmic and early stationary phases of growth (shake flask cultures). The results are shown in Tables 4-1 (Exp. 1) and 4-2 (Exp. 2). It can be seen that in two separate experiments the amount of a-amylase in the culture medium of ALK02732(pKTH277) was 1.5 to 2.5 fold the amount in the growth medium of ALK02732. Tables 4-1 and 4-2. The Effect of pKTH277 on a-amylase secretion of *B. amyloliquefaciens* (ALK02732).

TABLE 4-1

Experiment 1.

| | ALK02732 | | ALK02732 (pKTH277) | |
|---|---|---|---|---|
| TIME(h) | GROWTH* | α-AMYLASE (mg/l) | GROWTH* | α-AMYLASE (mg/l) |
| 3 | 106 | 1,1 | 100 | 1,1 |
| 4 | 241 | 8,8 | 240 | 8,8 |
| 5 | 426 | 47 | 430 | 72 |
| 6 | 520 | 160 | 525 | 224 |
| 7 | 576 | 480 | 580 | 650 |
| 8 | 625 | 800 | 630 | 1050 |

TABLE 4-2

Experiment 2.

| | ALK02732 | | ALK02732 (pKTH277) | |
|---|---|---|---|---|
| TIME(h) | GROWTH* | α-AMYLASE (mg/l) | GROWTH* | α-AMYLASE (mg/l) |
| 3 | 100 | 0,9 | 112 | 1,5 |
| 4 | 250 | 6 | 272 | 9 |
| 4,5 | 350 | 24 | 363 | 38 |
| 5 | 425 | 50 | 437 | 80 |
| 6,5 | 545 | 190 | 577 | 450 |
| 8 | 585 | 320 | 637 | 1300 |
| 12 | | | 702 | 1600 |
| 12,5 | 700 | 900 | | |

*The density of the culture as determined with the Klett-Summerson colorimeter using filter no. 66, indicated with Klett units.

Materials and Methods Used in this Example

Bacterial strains and plasmids: *B. amyloliquefaciens* strain ALK02732 (described by Vehmaanpera et al., 1991) was used in transformation and growth experiments.

ALK02732 (pKTH277) was made by transforming plasmid pKTH277 into ALK02732 (this study) and used in growth experiments. Plasmid pKTH277 carrying prsA gene is described by Kontinen et al. (1991).

Transformation of pKTH1277 into ALK02732 by electroporation: Plasmid pKTH277 was isolated using the alkaline lysis method and methylated with BamHI methylase (New England Biolabs) according to manufacturers instructions. About 0.5 µg of methylated plasmid DNA was used for electroporation. Electroporation was done as described by Vehmaanpera(1989). Cells were pulsed in 0.2 cm sample cuvettes (Bio-Rad Laboratories) with Gene Pulser™ apparatus (Bio-Rad Laboratories) set at 1.5 kV, 25 µF and 400Ω. Transformants were screened for chloramphenicol resistance on Luria-Kanamycin(10 µg/ml)-Chloramphenicol(5 µg/ml) plates. (Kanamycin was also on the plates to avoid loss of pKTH10, since ALK02732 contains pKTHIO, conferring kanamycin resistance).

Growth experiments and sample collection: First ALK02732 and ALK02732 (pKTH277) were grown over night on Luria plates. From the plates bacteria was added to 10 ml Luria and they were grown to logarithmic phase (Klett 100). Then 1 ml Glycerol (1/10 of cultivation volume) was added and cell suspension was frozen and stored in −70° C. Growth experiments were started by diluting Klett 100 cells 1:100 or 1:200 in 2×Luria+2% starch. The Luria used in growth experiments contained no salt. Cultivation volume was 20 ml and growth was in bottles in 37° C. with vigorous shaking. For both strains Kanamycin (10 µg/ml) and for ALK02732 (pKTH277) also Chloramphenicol (5 µg/ml) was supplemented to growth medium. The growth was indicated by measurements with Klett-Summerson colorimeter (Klett Manufacturing Co., Inc. N.Y.) using a number 66 filter. 0.5 ml samples were taken during growth, samples were centrifugated and culture supernatants were stored in −20° C. for α-amylase assays.

α-amylase assays: α-amylases in culture supernatants were determined using Phadebas tablets (Pharmacia). Samples were incubated for 1 h at 37° C. in 1 ml buffer (50 mM MES pH 6.8, 50 mM NaCl, 100 µM $CaCl_2$ containing ¼ dispersed phadebas tablet, after which 50 µl 5M NaOH was added to stop the reaction. After filtration through Whatman no.1 filter paper, absorbency of the filtrate was measured using 616–624 nm as an analytical wave length range and 800–804 nm as a reference wave length range. Commercially available α-amylase of B. amyloliquefaciens (Sigma) was used as a standard and results were expressed as mg enzyme per l.

References: Kontinen V., Saris P. and Sarvas M. (1991): A gene (prsA) of Bacillus subtilis involved in a novel, late stage of protein export. Mol. Microbiol. 5:1273–1283. Vehmaanpera, J. (1989): Transformation of Bacillus Amyloliquefaciens by electroporation. FEMS Microbiol. Lett. 61:165–170. VehmaanperaJ., Steinborn G. and Hofemeister J.(1991): Genetic manipulation of Bacillus amyloliquefaciens. J. Biotechnol. 9:221–240.

Example 3

Enhancement of Secretion of Subtilisin from B. lentus when there is Hyperexpression of PrsA Protein This example demonstrates the method and system of the invention in enhancing secretion of overexpressed exoproteins in B. lentus when the host gram-positive bacteria also hyperexpresses PrsA protein.

The effect of hyperexpression of prsA has been tested with respect to the secretion of subtilisin from B. lentus, commercially available as Experase™ and described in WO 89/06279 (in the name of Novo Nordisk A/S). The subtilisin is transcribed from the plasmid pPL1800 which is based on the expression vector pPL1759 (Hansen, C., Thesis, 1992, The Technical University of Denmark) with a pUB110 origin and the promoter and signal peptide from the alpha-amylase of B. licheniformis (amyL). The plasmid pSX94 is described in WO 89/06279. The B. subtilis strain SHa273 used for production is a protease weak derivative of DN1885 (Jorgensen, P. L. et al., (1991) FEMS Microbiol. Lett., 77:271–276), in which two additional proteases apr and npr have been inactivated. The secretion of the B. lentus subtilisin was measured from strains either with (MOL253) or without (MOL252) the prsA plasmid pKTH277, and growth was performed at 30° C. in soya broth BPX supplemented with kanamycin and chloramphenicol.

Measurements of subtilisin levels from the two strains after five days show that the strain with the prsA plasmid has a four fold higher secretion of the B. lentus subtilisin (160 micrograms/ml) compared to the strain without this plasmid (40 micrograms/ml).

The BPX medium used has the following composition:

| BPX: | Potato starch | 100 g/l |
| | Barley flour | 50 g/l |
| | BAN 5000 SKB | 0.1 g/l |
| | Sodium caseinate | 10 g/l |
| | Soy Bean Meal | 20 g/l |
| | $Na_2HPO_4$, 12 $H_2O$ | 9 g/l |
| | Pluronic | 0.1 g/l |
| Strain List: | | |
| B. subtilis | Genotype and properties | Parent strain |
| DN 1885 | amyE, amyR2 | RUB200 |
| PL1801 | amyE, amyR2, apr-, npr- | DN1885 |
| MOL252 | PL1801 (pPL1800) | PL1801 |
| MOL253 | PL1801 (pPL1800, pKTH277) | PL1801 |

The RUB 200 strain is described by Yoneda et al., 1979, Biochem Biophys. Res. Common. Vol. 91,1556–64.

Example 4

The Presence of PrsA Protein in Bacillus amyloliquefaciens and Bacillus subtilis The presence of PrsA protein has been demonstrated in two strains of B. amyloliquefaciens, strain ALK089 and strain ALK02100. Strain ALK089 is an industrial strain used for the production a-amylase. Strain ALK089 is an overproducer described in (Bailey, M. J. and Markkanen P. H. J. Appl. Chem. Biotechnol. 1975,25,73–79). Strain ALK02100 is a derivative of ATCC23843 (J. Vehmaanper a, FEMS Microbiology Letters 49(1988) 101–105).

The presence of PrsA protein has also been demonstrated in two strains of Bacillus licheniformis, strain 749/C (Pollock, M. R. (1965) Biochem. J. 94,666–6/5), and ATCC 14580.

The PrsA protein in these non Bacillus subtilis gram positive bacteria was identified using immunoblotting techniques. More specifically, cells collected at late exponential phase of growth (to minimize the amount of proteases—PrsA protein is protease sensitive) were immunoblotted, treated with lysozyme shortly (to make cell wall leaky, but again avoiding long treatment to minimize proteolysis), and solubilized at 100° C. with sample buffer containing 2% SDS. PrsA protein was detected with rabbit antiserum (KH1

283) raised against PrsA protein of *B. subtilis* produced in *Escherichia coli* (thus there was minimal antigenic cross reaction with any bacillar protein except PrsA). The antiserum detects nanogram amounts of *B. subtilis* like PrsA in the immunoblots.

In addition, all four strains were found to contain a protein of the size of PrsA of *B. subtilis*, and specifically identified by the above antiserum. The intensity of the staining of the band was approximately similar in both *B. amyloliquefaciens* strains and similar to that of PrsA protein in wild type *B. subtilis*. Coomassie Blue staining of parallel SDS-PAGE of cellular proteins of *B. amyloliquefaciens* showed only a very weak band at the position of PrsA protein like in the case of *B. subtilis* and consistent with PrsA protein of *B. amyloliquefaciens* being a minor cellular protein as it is in *B. subtilis*. The intensity of staining of the PrsA protein of the two *B. licheniformis* strains was weaker than in *B. subtilis*, suggesting a somewhat smaller amount of PrsA protein. However, it cannot be excluded that the weaker staining is due to less efficient binding of the antiserum of PrsA protein of *B. licheniformis* than to that of *B. subtilis*. Table 5 is a summary of the roughly estimated amount of PrsA in the different strains.

Table 5. Approximate amounts of PrsA protein found in cells of Bacillus strains during early stationary growth phase (at a cell density of Klett 400). Estimates are based on Western blots and are preliminary.

| Strain | PrsA in cells (arbitrary units) |
| --- | --- |
| *B. amyloliquefaciens* | |
| RH2078 | 4 |
| RH2079 | 4[1] |
| *B. licheniformis* | |
| RH2080 | 1 |
| RH 305 | 1 |
| *B. subtilis* | |
| IH6064 | 5 |
| IH6774[2] | 100[1] |

[1] Cells were collected from mid-logarithmic phase (at a density of Klett 100) of growth and the PrsA values estimated to correspond a density of Klett 400.
[2] This is an overproducer of PrsA, due to the content of pKTH277.

Materials and Methods Used in this Example

Strains: *Bacillus amyloliquefaciens* RH2078=ALKOB9=VTTI97=E18. This is an α-amylase overproducer. A gift from J.Vehmaanperä, ALKO. *Bacillus amyloliquefaciens* RH2079=ALK02100, derived from ALK02099 (pE 194/pC194). A gift from J. Vehmaanperä, ALKO. *Bacillus licheniformis* RH2080=BRA5=ATCCI4580. This is a producer of thermoresistent α-amylase. A gift from P. Saris, BI, H:ki. *Bacillus licheniformis* RH305=749/c. This is a penicillinase constitutive strain, originally derived from J. O. Lampen. *Bacillus subtilis* IH6074. This is metB5 sacA321. Ref. M. Sibakov et.al.1983. *Bacillus subtilis* IH6774. This is derived from IH6064, contains plasmids pKTH10 (carrying the α-amylase gene) and pKTH277(carrying the gene for coding PrsA).

Growth media: Luria-agar plates (L-plates); twice concentrated Luria-broth (2× L)

Purified PrsA protein: PrsA was purified from pKTH277 containing *B. subtilis* by M. Lauraeus.

Immune serum: *E. coli*-produced PrsA of *B. subtilis*, which was run in and cut out from a SDS-gel.

Chemicals: Phenylmethylsulfonylfluoride, Sigma P-7626. 100 mM in ethanol at −20° C. EDTA, Titriplex® III p.a. Merck 8418. As a 0.5M solution, pH 8. Lysozyme, Sigma L-6876. This was used as 1 mg/ml in the following solution: 2 mM potassium phosphate pH 7.15 mM $MgCl_2$, 20% sucrose. TCA 100% BCA† Protein Assay Reagent by Pierce. SDS-PAGE and Western Blot equipment and chemicals according to BioRad. Blots were stained with 4-chloro-1-naphtol.

Culture conditions and sample preparation for gel electrophoresis: Bacteria were grown on L-plates overnight at 37° C. Colonies were picked with a glass rod into a preweighed Eppendorf tube, and weighed. Sample buffer was added to get either 10 or 100 mg cells(ww)/ml. Samples were heated 10 min at 100° C.

Bacteria were grown in 2× L broth with agitation at 37° C. To minimize the protease effect bacteria (from −20° C.) were first grown to Klett 100 (corresponding to about 1–2 mg cells ww/ml, or about $10^9$ cells/ml). This was used as an inoculum at $10^{-2}$ dilution. 20 ml of bacteria were grown in Klett flasks and 4 ml samples were taken at Klett 100, at Klett 100+2 h (Klett appr.400), and at Klett 100+4 h (Klett appr.550).

Samples were immediately transferred into an ice bath, PMSF was added to 1 mM, and EDTA to 10 mM. Cells were separated from culture supernatant by centrifugation at 12000×g 10 min., and treated with lysozyme, 15 min at 37° C. in a 1/20 volume. An equal volume of sample buffer was added. Culture supernatant was precipitated in 10% TCA at 4° C. and concentrated 20-fold in sample buffer.

The samples were run in 12% SDS-PA gels, stained with Coomassie Brilliant Blue R, or blotted onto PVDF filters according to BioRad.

PrsA was detected with the specific anti-PrsA rabbit antiserum KH 1283.

Example 5

Enhanced Secretion of Lipase from *Pseudomonas mendocina* in *Bacillus subtilis* that Overproduces PrsA Protein Using the prsA gene in pKTH277, scientists at Genencor International, South San Francisco, Calif., USA, have shown that when *Bacillus subtilis* overexpresses both PrsA protein and lipase (from *Pseudomonas mendocina*, a gram-negative bacteria), the amount of lipase secreted into the medium is about 3.5 times greater than it is in controls that do not overexpress the prsA gene. The Genencor International scientists used industrial strains of Bacillus, and industrial fermentation conditions. (Data not shown).

Conclusion

Thus it can be seen that the present invention discloses a method and system for enhancing the production of industrially and medically important exoproteins in gram-positive bacteria. Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims. Various features of the invention are also evident from the following claims.

We claim:

1. An expression system for enhancing secretion of exoproteins in gram-positive bacteria engineered to express greater than wild-type amounts of PrsA protein from Bacillus, wherein said gram-positive bacteria express greater than wild-type amounts of at least one exoprotein of interest.

2. An expression system according to claim 1 wherein said PrsA protein is heterologous to said gram-positive bacteria.

3. An expression system according to claim 1, wherein said PrsA protein is PrsA protein from *Bacillus subtilis*, *Bacillus amyloliquefaciens* or *Bacillus licheniformis*.

4. An expression system according to claim 1 wherein said PrsA protein is present in said gram-positive bacteria in amounts that are from 2 to about 10 times greater than wild-type amounts.

5. An expression system according to claim 1 wherein said exoprotein of interest is a protease, a lipase, a cutinase, an amylase, a galactosidase, a pullulanase, a cellulase, a glucose isomerass, a protein disuphide isomerase, a CGT'ass (cyclodextrin gluconotransferase), a phytase, a glucose oxidase, a glucosyl transferase, laccase, bilirubin oxidase, a xylanase, an antigenic microbial or protozoan protein, a bacterial protein toxin, a microbial surface protein, a viral protein, a pharmaceutical.

6. An expression system according to claim 5 wherein said exoprotein of interest is a non native exoprotein that has been created by the addition of a signal sequence to the structural gene encoding said protein.

7. An expression system according to claim 1 wherein said gram-positive bacteria is a species of Bacillus.

8. An expression system according to claim 7 wherein said Bacillus is *Bacillus subtills*, *Bacillus licheniformis*, *Bacillus lentus*, *Bacillus brevis*, *Bacillus stearothermophllus*, *Bacillus alkalophilus*, *Bacillus amyloliquefeciens*, *Bacillus coagulans*, *Bacillus circulans*, *Bacillus lautus* and *Bacillus thuringlensis*.

9. A gram-positive bacteria expressing greater than wild-type amounts of at least one exoprotein of interest further comprising pKTH277.

10. A gram-positive bacteria expressing greater than wild-type amounts of at least one exoprotein of Interest and further comprising at least one of the following: (1) at least two copies of the prsA gene from *Bacillus subtilis*, (2) the prsA gone from *Bacillus subtilis*, operatively linked to strong regulatory sequences which result in overexpression of said prsA gene.

11. A gram-positive bacteria according to any of claims 9 or 10 wherein said gram-positive bacteria is a bacteria from the genus Bacillus.

12. A gram-positive bacteria according to claim 14 wherein said Bacillus is *Bacillus subtilis*, *Bacillus licheniformis*, *Bacillus lentus*, *Bacillus bravis*, *Bacillus stearothermophilus*, *Bacillus alkalophilus*, *Bacillus amylollquefaciens*, *Bacillus coagulans*, *Bacillus circulans*, *Bacillus lautus* and *Bacillus thuringlensis*.

13. A method for enhancing secretion of an exoprotein of interest in a gram-positive bacteria comprising expressing greater than wild type amounts of PrsA protein from Bacillus, in said gram-positive bacteria, wherein said gram-positive bacteria also expresses greater than wild type amounts of said exoprotein.

14. A method according to claim 13 wherein said gram-positive bacteria is a bacteria from the genus Bacillus.

15. A method according to claim 14 wherein said Bacillus bacteria is *Bacillus subtilis*, *Bacillus licheniformis*, *Bacillus lentus*, *Bacillus brevis*, *Bacillus stearothermophilus*, *Bacillus alkalophilus*, *Bacillus amyloliquefacions*, *Bacillus coagulans*, *Bacillus circulans*, *Bacillus lautus* or *Bacillus thuringlensis*.

16. An expression system for enhancing secretion of exoproteins in gram-positive bacteria comprising a gram-positive positive bacteria expressing greater than wild-type amounts of PrsA protein and expressing greater than wild-type amounts of at least one exoprotein of interest.

* * * * *

UNITED STATES PATENT AND TRADEMARK OFFICE
CERTIFICATE OF CORRECTION

PATENT NO. : 5,780,261
DATED : July 14, 1998
INVENTOR(S) : Vesa Kontinen, and Matti Sarvas It is certified that error appears in the above-identified patent and that said Letters Patent is hereby corrected as shown below:

Title page,
Inventor Vesa Kontinen home of record should read -- Lappeeranta, Finland --

Column 1,
Lines 61-62, "In this regard we recently discovered a novel component, the PrsA protein, of the secretion machinery of *B. subtilis*" should read -- In this regard a novel component of the secretion machinery of *B. subtilis* was recently discovered. This novel component is referred to as the PrsA protein. --.
Line 63, prior to "Kontinen" insert -- *See* --.
Line 63, delete the capital "L" in "*MicrobioL*" and insert a lower case l so as to read -- *Microbiol* --.
Line 64, italicize the term "et al.", to read -- *et al.* --.
Line 65, italicize the term "prsA", to read -- *prsA* --.

Column 2,
Line 2, italicize the term "prsA", to read -- *prsA* --.
Line 3, italicize the term "prsA", to read -- *prsA* --.
Line 3, delete "see" (not italicized) and insert -- *see* --.
Line 6, delete "etal." and insert -- *et al.* --.
Line 10, italicize the term "et al.", to read *et al.* --.
Line 11, italicize the term "et al.", to read *et al.* --.
Line 38, italicize the term "e.g." to read -- *e.g.* --.
Line 50, italicize the word "Bacillus", to read -- *Bacillus* --.

Column 3,
Line 7, italicize the term "i.e.", to read -- *i.e.* --.
Line 11, italicize the term "e.g." to read -- *e.g.* --.
Line 15, italicize the term "e.g." to read -- *e.g.* --.
Line 18, italicize the term "e.g." to read -- *e.g.* --.
Line 24, delete "capable of" and italicize the term "e.g.", to read -- *e.g.* -- and the word "Bacillus", to read -- *Bacillus* --.
Line 27, italicize the term "e.g." to read -- *e.g.* --.
Line 34, italicize the term "i.e.", to read -- *i.e.* --.
Line 43, italicize the term "prsA", to read -- *prsA* --.
Line 44, around "ies" in the word "antibodies" insert parenthesis so as to read -- antibod(ies) --.
Line 45, italicize the term "i.e.", to read -- *i.e.* --.
Line 47, delete one of two repetitions of the word "positive".

UNITED STATES PATENT AND TRADEMARK OFFICE
CERTIFICATE OF CORRECTION

PATENT NO. : 5,780,261
DATED : July 14, 1998
INVENTOR(S) : Vesa Kontinen, and Matti Sarvas It is certified that error appears in the above-identified patent and that said Letters Patent is hereby corrected as shown below:

Line 50, italicize the words "species of Bacilli", to read -- *species of Bacilli* --.
Line 67, after the sentence ending with "exoproteins of interest." insert the sentence -- The invention further includes exoproteins of interest that have been produced by menas of the methods and constructs of the present invention. --.

Column 4,
Line 3, delete the words "capable of".
Line 5, delete the words "capable of".
Line 9, delete the words "able to express" and insert -- expressing --.
Line 13, delete the words "able to express" and insert -- expressing --.
Line 16, italicize the term "prsA", to read -- *prsA* --.
Line 17, italicize the term "prsA", to read -- *prsA* --.
Line 19, delete the word "said" and insert the word -- *the* --.
Line 20, italicize the term "prsA", to read -- *prsA* --.
Line 22, italicize the term "prsA", to read -- *prsA* --.
Line 24, italicize the term "prsA", to read -- *prsA* --.
Line 25, italicize the term "prsA", to read -- *prsA* --.
Line 28, italicize the term "prsA", to read -- *prsA* --.
Line 35-36, delete the words "is also capable of expressing" and insert -- also expresses --.
Line 53, italicize the term "prsA", to read -- *prsA* --.
Line 66, after the last sentence on the page, that ends with the words "exoprotein of interest" insert the paragraph -- Still further, the invention includes exoproteins of interest produced by the constructs and methods of the present invention. --.

Column 5,
Line 17, italicize the term "i.e.", to read -- *i.e.* --.
Line 16, italicize the word "Bacillus", to read -- *Bacillus* --.
Line 27, italicize the word "Bacillus", to read -- *Bacillus* --.

Column 6,
Line 1, delete the word "virsu" and insert the word -- virus --.
Line 27, delete the term "etc." and insert the italicized word -- *et c.* --.
Line 60, italicize the term "prsA", to read -- *prsA* --.
Line 63, italicize the term "prsA", to read -- *prsA* --.
Line 66, italicize the term "prsA", to read -- *prsA* --.
Line 67, italicize the term "prsA", to read -- *prsA* --.

UNITED STATES PATENT AND TRADEMARK OFFICE
CERTIFICATE OF CORRECTION

PATENT NO. : 5,780,261
DATED : July 14, 1998
INVENTOR(S) : Vesa Kontinen, and Matti Sarvas Page 3 of 9

It is certified that error appears in the above-identified patent and that said Letters Patent is hereby corrected as shown below:

Column 7,
Line 5, delete the word "see" and insert the italicized word -- *see* --, italicize the term "et al." to read -- *et al.* --.
Line 11, italicize the word "Bacillus", to read -- *Bacillus* --.
Line 29, delete the term "recE4" and insert the italicized term -- *recE4* --.
Line 31, delete "(Dubnau et al., 1973: Keggins et al., 1978)".
Line 34, delete the word "gene" and insert the italicized word -- *gene* --.
Line 35, italicize the term "et al.", to read -- *et al.* --.
Line 46, delete the term "amyE" and insert the italicized term -- *amyE* --.
Lines 51-52, delete "Ortlepp et al., 1983:".
Line 52, italicize the term "et al.", to read -- *et al.* --.
Line 58, delete the word "etal" and insert the words -- *et al.* --" and delete the word "Gene." and insert the word -- *Gene.* --.
Line 60, delete the term "isS" and insert -- 1sS --.
Line 68, delete the word "etal" and insert the words -- *et al.* --
Line 69, between the words "Natl" and "Sci." insert the word -- Acad. --, and italicize the term "et al." to read -- *et al.* --.

Column 8,
Line 9, italicize the term "et al." to read -- *et al.* --.
Line 27, italicize the term "prsA", to read -- *prsA* --.
Line 28, italicize the term "prsA", to read -- *prsA* --.
Line 30, delete the term "b1aP" and insert the italicized term -- *blaP* --.
Line 38, italicize the term "prsA", to read -- *prsA* --.
Line 40, italicize the term "prsA", to read -- *prsA* --.
Line 42, italicize the term "prsA", to read -- *prsA* --.
Line 51, delete the term "amyE" and insert the italicized term -- *amyE* --.
Line 53, delete the word "DegO" and insert the word -- *DegQ* --.
Line 63, italicize the term "e.g.", to read -- *e.g.* --.

Column 9,
Line 2, italicize the word "Bacillus", to read -- *Bacillus* --.
Line 9, italicize the term "prsA", to read -- prsA --.
Line 14, delete one of two repetitions of the word "positive".
Line 15, italicize the term "prsA", to read -- *prsA* --.
Line 16, italicize the term "prsA", to read -- *prsA* --.
Line 18, italicize the term "prsA", to read -- *prsA* --.
Line 19, italicize the term "prsA", to read -- *prsA* --.

UNITED STATES PATENT AND TRADEMARK OFFICE
CERTIFICATE OF CORRECTION

PATENT NO.  : 5,780,261
DATED       : July 14, 1998
INVENTOR(S) : Vesa Kontinen, and Matti Sarvas It is certified that error appears in the above-identified patent and that said Letters Patent is hereby corrected as shown below:

Column 9 contd.
Line 20, italicize the term "prsA", to read -- *prsA* --.
Line 23, italicize the term "prsA", to read -- *prsA* --.
Line 29, italicize the term "prsA", to read -- *prsA* --.
Line 32, italicize the term "e.g.", to read -- *e.g.* --.
Line 53, italicize the term "prsA" both times it appears, to read -- *prsA* --.
Line 56, italicize the term "prsA", to read -- *prsA* --.
Line 60, italicize the term "prsA", to read -- *prsA* --.
Line 62, italicize the term "prsA", to read -- *prsA* --.
Line 63, italicize the term "prsA", to read -- *prsA* --.

Column 10,
Line 4, italicize the term "prsA" both times it appears, to read -- *prsA* --.
Line 6, italicize the term "prsA", to read -- *prsA* --.
Line 9, italicize the term "prsA", to read -- *prsA* --.
Line 17, italicize the word "Bacillus", to read -- *Bacillus* --.
Line 18, italicize the term "prsA", to read -- *prsA* --.
Line 20, delete ther "Sad" and insert the term -- *SacI* --.
Line 23, italicize the term "prsA", to read -- *prsA* --.
Line 24, italicize the term "prsA", to read -- *prsA* --.
Line 28, italicize the term "prsA", to read -- *prsA* --.
Line 34, italicize the term "prsA", to read -- *prsA* --.
Line 36, italicize the term "prsA", to read -- prsA --.
Line 60, delete the term "prs" and insert the italicized term -- *prs* --.
Line 67, italicise the term "et al.", to read -- *et al.* --.

Column 11,
Line 3, italicise the term "et al.", to read -- *et al.* --.
Line 4, italicise the term "et al.", to read -- *et al.* --.
Line 7, italicize the term "prsA", to read -- *prsA* --.
Line 9, italicize the term "prsA", to read -- *prsA* --.
Line 10, italicize the term "prsA", to read -- *prsA* --.
Line 12, delete the term "blaP" and insert the italicized the term -- *blaP* --.
Line 14, italicize the term "prsA", to read -- *prsA* --.
Line 15, delete the abbreviation "Gene." and insert the italicized abbreviation -- *Gene.* --.
Line 16, italicize the term "et al.", to read -- *et al.* --.
Line 18, italicize the term "et al.", to read -- *et al.* --.

UNITED STATES PATENT AND TRADEMARK OFFICE
CERTIFICATE OF CORRECTION

PATENT NO. : 5,780,261
DATED : July 14, 1998
INVENTOR(S) : Vesa Kontinen, and Matti Sarvas It is certified that error appears in the above-identified patent and that said Letters Patent is hereby corrected as shown below:

Column 11 contd.
Line 25, delete the term "amyL" and insert the italicized term -- *amyL* --.
Line 28, between the words "Natl." and "Sci.", insert the word -- Acad. --.
Line 28, italicize the term "et al.", to read -- et al. --
Line 37, delete the words "et al.", and insert the words -- *et al.* --.
Line 65, italicize the term "et al.", to read -- *et al.* --.

Column 12, Table 1,
Line (table) 1, column (table) 2, italicize the terms "metB5 sacA321", to read -- *metB5 sacA321* --.
Line (table) 2, column (table) 2, delete the term "metBS" and insert the italicized therm -- *metB5* -- and italicize the terms "his" and sacA321", to read -- *his metB5 sac321* --.
Line (table) 6, column (table) 2, italicize the terms "prs-29 metB5 sacA321", to read -- prs-29 metB5 sac321 --.
Line (table) 7, column (table) 3, delete the term "HIS 157", and insert the term -- *IH6157* --.
Line (table) 8, column (table) 2, italicize the terms "prs-40 metB5 sacA321", to read -- *prs-40 metB5 sacA321* --.
Line (table) 9, column (table) 2, italicize the terms "prs-3 metB5 sacA321", to read -- *prs-3 metB5 sacA321* --.
Line (table) 10, column (table) 2, italicize the terms "prs-40 metB5 sacA321", to read -- *prs-40 metB5 sacA321* --.
Line (table) 11, column (table) 2, italicize the terms "prs-II metB5 sacA321", to read -- *prs-II metB5 sacA321* --.
Line (table) 12, column (table) 2, italicize the terms "prs-13 metB5 sacA321", to read -- *prs-13 metB5 sacA321* --.
Line (table) 13, column (table) 2, italicize the terms "prs-33 metB5 sacA321", to read -- *prs-33 metB5 sacA321* --.
Line (table) 14, column (table) 2, italicize the terms "prs-26 metB5 sacA321", to read -- *prs-26 metB5 sacA321* --.
Line (table) 15, column (table) 2, italicize the terms "prs-13 metB5 sacA321", to read -- *prs-13 metB5 sacA321* --.
Line (table) 16, column (table) 2, italicize the terms "prs-26 metB5 sacA321", to read -- *prs-26 metB5 sacA321* --.
Line (table) 17, column (tble) 2, italicize the terms "prs-II metB5 sacA321", to read -- *prs-II metB5 sacA321* --.
Line (table) 19, column (tble) 2, italicize the terms "prs-13 metB5 sacA321", to read -- prs-13 metB5 sacA321 --.

UNITED STATES PATENT AND TRADEMARK OFFICE
CERTIFICATE OF CORRECTION

PATENT NO. : 5,780,261
DATED : July 14, 1998
INVENTOR(S) : Vesa Kontinen, and Matti Sarvas It is certified that error appears in the above-identified patent and that said Letters Patent is hereby corrected as shown below:

Column 12 contd.
Line (table) 20, column (table) 2, italicize the terms "prs-II metB5 sacA321", to read -- *prs-II metB5 sacA321* --.
Line (table) 24, column (table) 2, italicize the terms "prs-29 metB5 sacA321", to read -- *prs-29 metB5 sacA321* --.
Line (table) 34, column (table) 2, italicize the terms "arg(GH)15, leuA8, rm-, recE4" to read -- *arg(GH)15, leuA8, rm-, recE4* --.
Line (table) 35, column (table) 2, italicize the terms "stp, thrA", to read -- stp, thrA --.
Line (table) 36, column (table) 2, italicize the terms "hisA1 thr-5 trpC2" to read -- *his A1 thr-5 trpC2* --.
Line (table) 37, column (table) 2, before the φ symbol, delete the two colons, and insert an open parenthesis -- ( -- and italicize the term "amyE" to read -- *amyE* --.
The second heading of column 1 after the segment with the heading "B. Subtilis", delete the column label "*B. Subtilis*" and insert the italicized column label -- *B. Subtilis* --.
Line (table) 41, first line under the second heading titled "*B.Subtilis*, prior to the term "pKTH1601", delete the two colons, and insert an open parenthesis -- ( --, and in the third column of the table italicize the term "et al." to read -- *et al.* --.
Line (table) 42, in the second line under the second heading titled "*B. Subtilis*, prior to the term "pKTH3200", delete the two colons, and insert an open parewnthesis -- ( --.
Under heading *E.coli*, line 55, column (table) 3 delete the term "TG1" and insert the term -- TGI --.
Under heading *E.coli*, line 56, column (table) 3 delete the term "EHI" and insert the term -- EH1679 --.
Footnote 1, line 65, fdelete the term "decQ" and insert the italicized term -- *decQ* --, and delete the word "dreivative" and insert the word -- derivative --.

Column 13, Table 2,
Line (table) 1, column (table) 2, italicize the terms "amyE neo", to read -- *amyE neo* --.
Line (table) 2, column (table) 3, italicize the term "et al.", to read -- *et al.* --.
Line (table) 3, column (table) 2, italicize the terms "prsA bla", to read -- *prsA bla* --.
Line (table) 4, column (table) 3, italicize the terms "et al.", to read -- *et al.* --.
Line (table) 5, column (table) 2, italicize the terms "prsA cat ermC", to read -- *prsA cat ermC* --.
Line (table) 6, column (table) 2, italicize the terms "amyL neo", to read -- *amyL neo* --.
Line (table) 8, column (table) 2, italicize the terms "degQ neo", to read -- *degQ neo* --.
Line (table) 9, column (table) 2, italicize the terms "bla cat neo" to read -- *bla cat neo* --.
Line (table) 11, column (table) 2, italicize the terms "prsA bla", to read -- *prsA bla* --.

UNITED STATES PATENT AND TRADEMARK OFFICE
CERTIFICATE OF CORRECTION

PATENT NO.   : 5,780,261
DATED        : July 14, 1998
INVENTOR(S)  : Vesa Kontinen, and Matti Sarvas It is certified that error appears in the above-identified patent and that said Letters Patent is hereby corrected as shown below:

Column 13, Table 2, contd.
Line (table) 12, column (table) 2, italicize the terms "prsA bla", to read -- prsA bla --.
Line (table) 13, column (table) 2, italicize the term "ermC", to read -- *ermC* --.
Line (table) 14, column (table) 2, italicize the terms "prsA ermC, to read --
*prsA ermC* --.
Line (table) 15, column (table) 2, italicize the term "prs cat ermC", to read -- *prsA cat ermC* --.
Line (table) 16, column (table) 2, italicize the term "prsA", to read -- *prA* --.
Line (table) 17, column (table) 2, italicize the term "cat ermC", to read -- *cat ermC* --.
Line (table) 18, column (table) 2, italicize the term "bla cat tet", to read -- *bla cat tet* --.
Line (table) 19, column (table) 2, italicize the term "subC cat", to read -- *subC cat* --.
Line (table) 20, column (table) 3, italicize the term ""et al.", to read -- *et al.* --.
Line (table) 22, column (table) 3, after the year "1990" insert a close parenthesis -- ) --.

Column 13, Table 3,
Heading for column 2 (table) delete the word "in" after the word "gene" and insert the words -- located on a --.
Footnoite a, line 55, delete the term "amyE" and insert the italicized term -- *amyE* --.

Column 17,
Line 58, delete the term "1H6774" and insert the term -- IH6774 --.

Column 18,
Line 43, italicize the term "prsA", to read -- *prsA* --.
Line 49, italicize the term "prsA", to read -- *prsA* --.
Line 50, italicize the word "Bacillus", to read -- *Bacillus* --.

Column 19, claim 1,
Italicize the word "Bacillus", to read -- *Bacillus* --.

Column 19, claim 5,
Delete the term "CGT'ass" and insert the term -- CGT'ase --.

Column 19, claim 7,
Italicize the word "Bacillus", to read -- *Bacillus* --.

UNITED STATES PATENT AND TRADEMARK OFFICE
CERTIFICATE OF CORRECTION

PATENT NO. : 5,780,261
DATED : July 14, 1998
INVENTOR(S) : Vesa Kontinen, and Matti Sarvas It is certified that error appears in the above-identified patent and that said Letters Patent is hereby corrected as shown below:

Column 19, claim 8, contd.
Line 31, delete the word "subtills", and insert the word -- *subtilis* --, and italicize the word "Bacillus", to read -- *Bacillus* --.
Line 33, delete the word "amyloliquefeciens", and insert the word -- *amyloliquefaciens* --.
Line 35, delete the word "thuringlesis", and insert the word -- *thuringiensis* --.

Column 20, claim 10,
Line 2, delete the word "Interest", and insert the word -- interest --.
Line 4, italicize the term "prsA", to read -- *prsA* --.
Line 5, italicize the term "prsA", to read -- *prsA* --.
Line 7, italicize the term "prsA", to read -- *prsA* --.

Column 20, claim 11,
Line 10, italicize the word "Bacillus", to read -- *Bacillus* --.

Column 20, claim 12,
Line 10, delete the word "claim 14", and insert the word -- claim 11 --.
Line 12, italicize the word "Bacillus", to read -- Bacillus --.
Line 13, delete the word "bravis", and insert the word -- *brevis* --.
Line 15, delete the word "amylolliquefaciens", and insetr the word -- *amyloliquefaciens* --.
Line 16, delete the word "thuringlesis", and insert the word -- *thuringiensis* --.

Column 20, claim 13,
Line 20, italicize the word "Bacillus", to read -- *Bacillus* --.

Column 20, claim 14,
Line 24, italicize the word Bacillus", to read -- *Bacillus* --.

Column 20, claim 15,
Line 25, italicize the word Bacillus", to read -- *Bacillus* --.

UNITED STATES PATENT AND TRADEMARK OFFICE
CERTIFICATE OF CORRECTION

PATENT NO. : 5,780,261
DATED : July 14, 1998
INVENTOR(S) : Vesa Kontinen, and Matti Sarvas It is certified that error appears in the above-identified patent and that said Letters Patent is hereby corrected as shown below:

Column 20, claim 15 contd.
Line 28, delete the word "amylolliquefaciens", and insetr the word -- *amyloliquefaciens* --.
Line 30, delete the word "thuringlesis", and insert the word -- *thuringiensis* --.

Column 20, claim 16,
Line 33, delete one of two repetitions of the word "positive".

Signed and Sealed this

Twenty-seventh Day of November, 2001

Attest:

NICHOLAS P. GODICI